United States Patent [19]

Brunelle et al.

[11] 4,217,438

[45] Aug. 12, 1980

[54] POLYCARBONATE TRANSESTERIFICATION PROCESS

[75] Inventors: Daniel J. Brunelle, Scotia; William E. Smith, Schenectady, both of N.Y.

[73] Assignee: General Electric Company, Schenectady, N.Y.

[21] Appl. No.: 970,058

[22] Filed: Dec. 15, 1978

[51] Int. Cl.$^2$ .......................................... C08G 63/62
[52] U.S. Cl. .................................. 528/202; 260/463; 525/462; 528/125; 528/167; 528/171; 528/196; 528/205; 528/370; 528/401
[58] Field of Search ............... 528/202, 196, 401, 370, 528/371; 260/463

[56] References Cited

U.S. PATENT DOCUMENTS

| | | | |
|---|---|---|---|
| 3,321,439 | 5/1967 | Bollert et al. | 528/202 |
| 3,442,854 | 5/1969 | Curtius et al. | 528/202 |

*Primary Examiner*—Theodore E. Pertilla
*Attorney, Agent, or Firm*—F. Wesley Turner; James C. Davis, Jr.; Leo I. MaLossi

[57] ABSTRACT

A polycarbonate process comprising contacting in the presence of a base, a β-fluoroaliphatic carbonate, and a polyhydroxy compound selected from alcohols and/or phenols. The resulting polycarbonates are useful as polycarbonates per se, or useful in the preparation of high molecular weight polycarbonates which can be molded or formed into films, laminates or reinforced plastics by conventional techniques.

10 Claims, No Drawings

POLYCARBONATE TRANSESTERIFICATION PROCESS

CROSS REFERENCE TO RELATED APPLICATIONS

This invention is related to copending U.S. patent application Ser. Nos. 969,682 of J. E. Hallgren and W. E. Smith, and 969,683 of D. J. Brunelle and W. E. Smith both filed Dec. 15, 1978. The aforesaid applications are assigned to the same assignee as the assignee of this application and all the disclosures contained therein are hereby incorporated herein in their entirety by reference.

BACKGROUND OF THE INVENTION

1. Field of the Invention

This invention relates to a polycarbonate process comprising contacting in the presence of a base, a β-fluoroaliphatic carbonate and a polyfunctional hydroxy compound selected from alcohols and/or phenols.

2. Description of the Prior Art

In general, the prior art including The Encyclopedia of Polymer Science, Vol. 10 (1969), Chemistry and Physics of Polycarbonates, Polymer Reviews, H. Schnell, Vol. 9, John Wiley and Sons, Inc. (1964) reports that transesterification of aliphatic hydroxy compounds with carbonic acid aliphatic or aromatic diesters occurs readily in the presence of a basic catalyst and is a convenient method of synthesis of higher carbonates. Heretofore, to the best of our knowledge, the efficient transesterification of a polyfunctional phenol with a carbonic acid aliphatic diester in the substantial absence of undesirable side reactions has not been reported.

Unaccountably and nonanalogous with the practice of this invention, transesterification of a polyfunctional phenol with a carbonic acid β-fluoroaliphatic diester occurs, whereas transesterification with a chloroaliphatic diester does not occur.

Further, unexpectedly when a phenolic reactant and a bis(β-fluoroaliphatic) carbonate, also commonly referred to as a carbonic acid aliphatic diester, is contacted in the presence of a base, ester interchange (also commonly referred to as re-, trans- or inter-esterification) occurs resulting in the formation of an aromatic polycarbonate and a β-fluoroaliphatic alcohol. Generally and further unexpectedly, only small amounts of carbonic acid aliphatic-aromatic mixed diester is associated with the isolated aromatic polycarbonate reaction products.

DESCRIPTION OF THE INVENTION

This invention embodies a polycarbonate process comprising contacting in the presence of a base, a β-fluoroaliphatic carbonate, and a polyfunctional hydroxy compound selected from alcohols and/or phenols. The process reactants and the resulting reaction products can be illustrated by Equation (I) which is furnished for exemplary purposes only—since the bis(β-fluoroaliphatic) carbonate reactant and the reaction mechanism(s) involved in the preparation of the polycarbonates can be different and more complex:

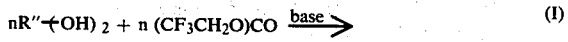  (I)

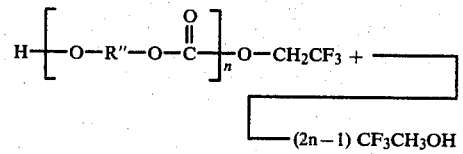

wherein independently R″ is an alkylene, cycloalkylene or arylene radical, and n is a number equal to at least 1. In a preferred embodiment R″ is a predominantly—and often exclusively—an arylene radical.

A polyhydroxy alcohol is defined herein and in the appended claims as any polyhydroxy-substituted aliphatic including cycloaliphatic compounds. Illustratively, a polyhydroxy alcohol or alcoholic reactant can be described by the formula

  (II)

wherein $R_a$ represents an aliphatic radical and —OH radicals are attached directly to aliphatic ring carbon atoms, x being a number at least equal to 2. The $R_a$ radical can be any aliphatic alcohol including linear, branched, cross-linked or graft alkanols, also including—but not limited thereto—carbo- or heteromonocyclic, polycyclic or fused polycyclic alcohol systems which are connected to each other by single or double valence bonds or bi- or multi-valent radicals.

Presently preferred saturated aliphatic alcoholic reactants are of the general formula:

$$C_nH_{2n+2-z}(OH)_z,$$  (III)

wherein n is a whole number of from 1–30, preferably 1–20, and still more preferably 1–10, and wherein z is a whole number of 2–4, preferably from 2–3, and more preferably 2. Illustrative alcohols follow 1,2-ethanediol (ethylene glycol); 2,2-oxydiethanol (diethylene glycol); triethylene glycol; tetraethylene glycol; 1,2-propanediol (propylene glycol); dipropylene glycol; 1,3-propanediol; 1,4-butanediol; 1,5-pentanediol; glycerol (1,2,3-propanetriol); 1,1,1-trimethylolethane (2-hydroxymethyl-2-methyl-1,3-propanediol); 1,1,1-trimethylolpropane (2-ethyl-2-hydroxymethyl-1,3-propanediol); pentaerythritol (2,2-bis(hydroxymethyl)-1,3-propanediol); sorbitol (D-glucitol); 1,2,6-hexanetriol; methyl glucoside, etc.

A polyhydroxy phenol is defined herein and in the appended claims as any polyhydroxy-substituted aromatic compound. Illustratively, a polyhydroxy-substituted aromatic or phenolic reactant can be described by the formula:

  (IV)

wherein $R_b$ represents an aromatic radical and —OH radicals are attached directly to aromatic ring carbon atoms, x being a number at least equal to 2. The $R_b$ radical can be carbo- or heteromonocyclic, polycyclic, or fused polycyclic, and can have two or more cyclic systems (monocyclic, polycyclic or fused polycyclic systems) which are connected to each other by single or double valence bonds, or bi- or multivalent radicals.

Presently preferred dihydroxy substituted aromatic reactants are of the general formula:

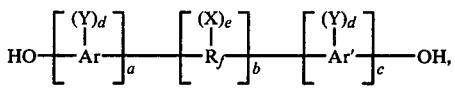

wherein $R_f$ is an alkylene, alkylidene, cycloalkylene, cycloalkylidene or arylene linkage or a mixture thereof, a linkage selected from the group consisting of ether, carbonyl, amine, a sulfur or phosphorus containing linkage, Ar and Ar' are arene radicals, Y is a substituent selected from the group consisting of organic, inorganic and organometallic radicals, X is halogen or a monovalent hydrocarbon group selected from the class consisting of alkyl, aryl and cycloalkyl and combinations thereof, d represents a whole number of at least 0 up to a maximum equivalent to the number of replaceable hydrogens substituted on the aromatic rings comprising Ar or Ar', e represents a whole number of from 0 to a maximum controlled by the number of replaceable hydrogens on $R_f$, a, b and c represent whole numbers including 0, when b is not zero, neither a or c may be zero, otherwise either a or c but not both may be 0, when b is zero, the aromatic groups can be joined by direct carbon bonds.

Even more preferred are dihydroxy aromatic reactants of the formulae:

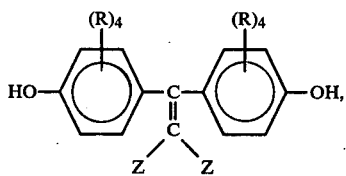

where independently each R is hydrogen, chlorine, bromine or a $C_{1-30}$ monovalent hydrocarbon or hydrocarbonoxy group, each Z is hydrogen, chlorine or bromine, subject to the proviso that at least one Z is chlorine or bromine, and

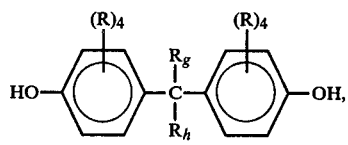

where independently each R is as defined hereinbefore, and independently $R_g$ and $R_h$ are hydrogen or a $C_{1-30}$ monovalent hydrocarbon group.

Specific examples of some members of the above class of dihydroxy aromatic reactants—which are presently preferred—follow:

resorcinol;
4,4'-dihydroxy-diphenyl;
1,6-dihydroxy-naphthalene;
2,6-dihydroxy-naphthalene;
4,4'-dihydroxy-diphenyl methane;
4,4'-dihydroxy-1,1-ethane;
4,4'-dihydroxy-diphenyl-1,1-butane;
4,4'-dihydroxy-diphenyl-1,1-isobutane;
4,4'-dihydroxy-diphenyl-1,1-cyclopentane;
4,4'-dihydroxy-diphenyl-1,1-cyclohexane;
4,4'-dihydroxy-diphenyl-phenyl methane;
4,4'-dihydroxy-diphenyl-2-chlorophenyl methane;
4,4'-dihydroxy-diphenyl-2,4-dichlorophenyl methane;
4,4'-dihydroxy-diphenyl-p-isopropylphenyl-methane;
4,4'-dihydroxy-diphenylnaphthyl methane;
4,4'-dihydroxy-diphenyl-2,2-propane;
4,4'-dihydroxy-3-methyl-diphenyl-2,2-propane;
4,4'-dihydroxy-3-cyclohexyl-diphenyl-2,2-propane;
4,4'-dihydroxy-3-methoxy-diphenyl-2,2-propane;
4,4'-dihydroxy-3-isopropyl-diphenyl-2,2-propane;
4,4'-dihydroxy-3,3'-dimethyl-diphenyl-2,2-propane;
4,4'-dihydroxy-3,3'-dichloro-diphenyl-2,2-propane;
4,4'-dihydroxy-diphenyl-2,2-butane;
4,4'-dihydroxy-diphenyl-2,2-pentane;
4,4'-dihydroxy-diphenyl-2,2(4-methyl pentane);
4,4'-dihydroxy-diphenyl-2,2-n-hexane;
4,4'-dihydroxy-diphenyl-2,2-nonane;
4,4'-dihydroxy-diphenyl-4,4-heptane;
4,4'-dihydroxy-diphenyl phenylmethyl methane;
4,4'-dihydroxy-diphenyl-4-chlorophenylmethyl methane;
4,4'-dihydroxy-diphenyl-2,5-dichlorophenylmethyl methane;
4,4'-dihydroxy-diphenyl-3,4-dichlorophenylmethyl methane;
4,4'-dihydroxy-diphenyl-4-fluorophenylmethyl methane;
4,4'-dihydroxy-diphenyl-2-naphthylmethyl methane;
4,4'-dihydroxy-tetraphenyl methane;
4,4'-dihydroxy-diphenyl phenylcyano methane;
4,4'-dihydroxy-diphenyl-1,2-ethane;
4,4'-dihydroxy-diphenyl-1,6(1,6-dioxo-n-hexane);
4,4'-dihydroxy-diphenyl-1,10(1,10-dioxo-n-decane);
bis-p-hydroxy-phenylether-4,4'-diphenyl;
$\alpha,\alpha,\alpha',\alpha'$-tetramethyl-$\alpha,\alpha'$-(di-p-hydroxyphenyl)-p-xylylene;
$\alpha,\alpha,\alpha',\alpha'$-tetramethyl-$\alpha,\alpha'$-(di-p-hydroxyphenyl)-m-xylylene;
2,2'-dihydroxy-3,3',5,5'-tetramethyldiphenyl methane;
4,4'-dihydroxy-3,3'-dimethyl-diphenyl methane;
4,4'-dihydroxy-2,2'-dimethyl-diphenyl methane;
4,4'-dihydroxy-3,3',5,5'-tetramethyl-diphenyl methane;
4,4'-dihydroxy-3,3'-dichloro-diphenyl methane;
4,4'-dihydroxy-3,3'-dimethoxy-diphenyl methane;
4,4'-dihydroxy-2,2',5,5'-tetramethyl-diphenyl methane;
4,4'-dihydroxy-2,2',3,3',5,5',6,6'-octamethyl-diphenyl methane;
4,4'-dihydroxy-2,2'-dimethyl-5,5'-diisopropyl-diphenyl methane;
4,4'-dihydroxy-2,2'-dimethyl-5,5'-dipropyl-diphenyl methane;
4,4'-dihydroxy-2,2'-dimethyl-5,5'-di-tert.-butyl-diphenyl methane;
4,4'-dihydroxy-diphenyl-5,5-nonane;
4,4'-dihydroxy-diphenyl-6,6-undecane;
4,4'-dihydroxy-diphenyl-3,3-butanone-2;
4,4'-dihydroxy-3,3'-dimethyl-diphenyl-3,3-butanone-2;
4,4'-dihydroxy-diphenyl-4,4-hexanone-3;
4,4'-dihydroxy-diphenyl ether;
4,4'-dihydroxy-diphenyl sulfide;
4,4'-dihydroxy-3,3'-dimethyldiphenyl sulfide;
4,4'-dihydroxy-diphenyl sulfoxide;
4,4'-dihydroxy-diphenyl sulfone;
4,4'-dihydroxy-3,3'-dichlorodiphenyl sulfone;
4,4'-dihydroxy-3,3',5,5'-tetramethyl-diphenyl methane;
4,4'-dihydroxy-3,3',5,5'-tetrachloro-diphenyl-1,1-cyclohexane;
4,4'-dihydroxy-3,3',5,5'-tetrachloro-diphenyl-2,2-propane;

4,4'-dihydroxy-3,3',5,5'-tetramethyl-2,2',6,6'-tetrabromo-diphenyl-2,2-propane; and
4,4'-dihydroxy-3,3',5,5'-tetrabromo-diphenyl-2,2-propane;
1,1-dibromo-2,2-bis(4-hydroxyphenyl)ethylene;
1,1-dichloro-2,2-bis(5-methyl-4-hydroxyphenyl)ethylene;
1,1-dibromo-2,2-bis(3,6-n-butyl-4-hydroxyphenyl)ethylene;
1,1-dichloro-2,2-bis(2-chloro-5-ethyl-4-hydroxyphenyl)ethylene;
1,1-dibromo-2,2-bis(2,5-dibromo-4-hydroxyphenyl)ethylene;
1-bromo-2,2-bis(4-hydroxyphenyl)ethylene;
1-chloro-2,2-bis(3,5-di-isopropyl-4-hydroxyphenyl)ethylene;
1-bromo-2,2-bis(2,6-di-t-butyl-4-hydroxyphenyl)ethylene;
1-chloro-2,2-bis(2,6-dichloro-4-hydroxyphenyl)ethylene;
1-bromo-2,2-bis(2,3-dibromo-4-hydroxyphenyl)ethylene;
1,1-dichloro-2,2-bis(3,5-dichloro-4-hydroxyphenyl)ethylene;
1,1-dichloro-2,2-bis(3,5-dibromo-4-hydroxyphenyl)ethylene;
1,1-dibromo-2,2-bis(5-chloro-4-hydroxy)ethylene;
1-chloro-2,2-bis(3,6-dibromo-4-hydroxyphenyl)ethylene;
1-bromo-2,2-bis(2-chloro-4-hydroxyphenyl)ethylene;
1,1-dichloro-2,2-bis(2,3,5-trichloro-4-hydroxyphenyl)ethylene;
1,1-dibromo-2,2-bis(2,3,5,6-tetrabromo-4-hydroxyphenyl)ethylene;
1-chloro-2,2-bis(3-phenyl-4-hydroxyphenyl)ethylene;
1-bromo-2,2-bis(3,5-diphenyl-4-hydroxyphenyl)ethylene;
1,1-dichloro-2,2-bis(2,6-diphenyl-4-hydroxyphenyl)ethylene;
1,1-dibromo-2,2-bis(3-bromo-5-phenyl-4-hydroxyphenyl)ethylene;
1-chloro-2,2-bis(3-methoxy-4-hydroxyphenyl)ethylene;
1-bromo-2,2-bis(3,5-dimethoxy-4-hydroxyphenyl)ethylene;
1,1-dichloro-2,2-bis(2-ethoxy-4-hydroxyphenyl)ethylene;
1,1-dibromo-2,2-bis(2,6-diethoxy-4-hydroxyphenyl)ethylene;
1-chloro-2,2-bis(5-phenylether-4-hydroxyphenyl)ethylene;
1-bromo-2,2-bis(3,5-diphenylether-4-hydroxyphenyl)ethylene; and
1,1-dichloro-2,2-bis(3-chloro-5-phenylether-4-hydroxyphenyl)ethylene.

Any β-fluoroaliphatic carbonate can be used in our process and is defined herein in the appended claims as a "β-fluoroaliphatic carbonate". Illustratively, the β-fluoroaliphatic carbonate reactant can be described by the generic formula:

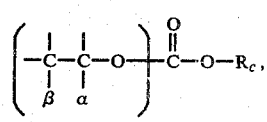

(VIII)

which describes the essential features of a β-fluoroaliphatic carbonate reactant, i.e. a carbonate class wherein at least two oxy groups are both independently and directly bonded to the same carbonyl carbon atom subject to the proviso that at least one of the oxy groups is separated from at least one fluorine atom by at least two aliphatic carbon atoms, $R_c$ being a

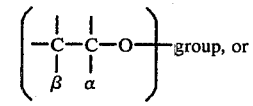

an alkyl, a cycloalkyl, or aryl radical, including combinations thereof. Further, illustratively the β-fluoroaliphatic carbonates can be saturated, unsaturated, linear, branched, etc. in skeletal form. Further the β-fluoroaliphatic carbonates can be carbo- or hetero-monocyclic, polycyclic or fused polycyclic and can have two or more cyclic systems (monocyclic, polycyclic or fused polycyclic systems) which are connected to each other by single or double valence bonds or multivalent radicals. Further, presently preferred β-fluoroaliphatic carbonates contain from 4–25, and more preferably 4–15 carbon atoms. Illustrative β-fluoroaliphatic carbonates include the following:

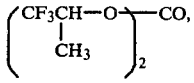
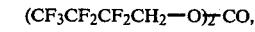
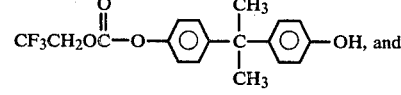
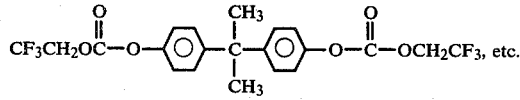

The process can be carried out in the absence of any solvent, e.g. where the alcohol, phenol and/or β-fluoroaliphatic carbonate act(s) as both reactant and solvent. The process can also be carried out in the presence of a nonpolar or low to medium polar solvent subject to the proviso, more preferably, that the solvent employed be substantially free of protic solvents, especially protic solvents capable of strong hydrogen bonding. In general, among presently preferred solvents are the following:

(A) non- or low-polar solvents such as hexane, 3-methylpentane, heptane, cyclohexane, methylcyclohexane, cyclohexane, isooctane, p-cymene, cumene, decalin, toluene, xylene benzene, diethylether, diphenyl ether, dioxane, thiophene, dimethylsulfide, ethyl acetate, tetrahydrofuran, etc., and mixtures thereof, and (B) medium-polarity solvents such as chlorobenzene, anisol, bromobenzene, dichlorobenzenes, methyl formate, iodobenzene, acetone, acetophenone, etc., and mixtures thereof.

Although not limiting the process of this invention or the scope thereof to any theory, we believe that the process rate constant is associated with the polarity and dielectric strengths of the solvent employed. It is also believed that a proton-transfer reaction is involved which is significantly effected by the solvent in its initial and transition state. Accordingly, in general, it is believed desirable that the solvent employed be selected from the group consisting of any nonpolar or polar solvent class which solvent classes are characterized as classes of solvents substantially free of high dielectric constant values, i.e. solvents incapable of strong hydrogen bonding to phenolic reactants or any intermediates derived therefrom during the course of the reaction. In general, solvents which are preferably excluded from the reaction medium are polar protic solvents characterized as solvent species which have the capability of donating strong hydrogen bonding to solute species and which have high dielectric constants, e.g. dielectric constants of from about 20 to about 50 or even higher. Non- or low-polar solvents as defined herein are characterized in accordance with the solvent polarity scales described in Solute-Solvent Interactions, J. F. Kotese and K. D. Richey (1969) Marcel Dekker, pages 281–282.

In general, the process can be carried out in any basic reaction medium, preferably that provided by the presence of any inorganic or organic base.

Representative of basic species which can be employed are the following: elemental alkali and alkaline earth metals; basic quaternary ammonium, quaternary phosphonium or tertiary sulfonium compounds; alkali or alkaline earth metal hydroxides; salts of strong bases and weak organic acids; primary, secondary or tertiary amines; etc. Specific examples of the aforementioned are sodium, potassium, magnesium metals, etc.; quaternary ammonium hydroxide, tetraethyl phosphonium hydroxide, etc.; sodium, potassium, lithium, and calcium hydroxide; quaternary phosphonium, tertiary sulfonium, sodium, lithium and barium carbonate, sodium acetate, sodium benzoate, sodium methylate, sodium thiosulfate; sodium compounds, e.g. sulfide, tetrasulfide, cyanide, hydride and borohydride; potassium fluoride, methylamine, isopropylamine, methylethylamine, allylethylamine, ditertbutylamine, dicyclohexylamine, dibenzylamine, tert-butylamine, allyldiethylamine, benzyldimethylamine, diactylchlorobenzylamine, dimethylphenethylamine, 1-dimethylamino-2-phenylpropane, propanediamine, ethylenediamine, N-methylethylenediamine, N,N'-dimethylethylenediamine, N,N,N'-tritertbutylpropanediamine, N,N',N',N''-tetramethyldiethylenetriamine, pyridine, aminomethylpyridines, pyrrole, pyrrolidine, piperidine, 1,2,2,6,6-pentamethylpiperidine, imidazole, etc. Especially preferred bases are the hydroxides of lithium, sodium, potassium, calcium or barium hydroxide; sodium, lithium or barium carbonate, sodium acetate, sodium benzoate, sodium methylate, lithium, sodium or potassium, etc., phenoxide; lithium, sodium or potassium, etc., salts of bisphenol-A, 2,2,2-trifluoroethoxide, β-trifluoroethanol, etc., including mixtures thereof.

Any amount of base can be employed. In general, effective mole ratios of base to polyfunctional hydroxy compounds are within the range of from about $10^{-6}$ to 1 or even lower to about 1 to 1, or even higher, preferably from $10^{-4}$ to 1 to about 0.02 to 1, and more preferably from $10^{-3}$ to 1 to 0.01 to 1. Generally, mole ratios of at least $10^{-3}$ to 1 enhances both the reaction rate and the yield of polycarbonates.

Any reaction temperature can be employed. Optimum reaction temperatures are generally within the range of from 80° C. or even lower, to 300° C. or even higher, and more often 120° C. to 200° C.

Any reaction pressure can be employed, e.g. atmosphere, subatmosphere or superatmospheric. Generally, however, in the preparation of high molecular weight polycarbonates, the process is preferably carried out under a reaction pressure of approximately 1 atm. (~760 mm. Hg.) during the initial phase of the reaction with a subsequent pressure reduction to values in the order of 50 to 100 mm. Hg. (vacuum), or even lower.

Any reaction time can be employed. Generally, optimum reaction time periods are from about 0.5 hours or even less to about 24 hours or even more.

Any amount of solvent can be employed. In general, optimum solvent to polyfunctional hydroxy compound mole proportions are from 0 to 10, preferably from 0 to 1.

In order that those skilled in the art may better understand my invention, the following examples are given which are illustrative of the best mode of this invention, however, these examples are not intended to limit the invention in any manner whatsoever. In the examples, unless otherwise specified all parts are by weight and the reaction product identities were verified by spectroscopic techniques and/or comparison with authentic materials.

EXAMPLE I

Procedure for the preparation of bis(2,2,2-trifluoroethyl) carbonate which is not an example of this invention.

Phosgene gas was bubbled into a 500 ml. 3-neck flask containing 300 ml. of dry ether at 0° C. until 25 g. (.25 mole) had been added. To this solution at 0° C. was added a solution of 50 g. (0.5 mole) of 2,2,2-trifluoroethanol and 40.3 ml. (0.5 mole) of pyridine in 100 ml. of ether. The addition was carried out over 3 hrs., forming a thick white precipitate. The reaction was then warmed to room temperature and was stirred for one hour. The precipitate was removed by suction filtration, washed with ether. The ether was removed by distillation, and the product was distilled (b.p.=58°/70 mm.; 113°/760 mm.), to yield 49.5 g. (88%) of bis(2,2,2-trifluoroethyl) carbonate.

EXAMPLE II

A 25 ml. flask was charged with 1.14 g. (5 mmol.) of bisphenol-A, i.e.—also abbreviated hereafter as "BPA"—bis(4-hydroxyphenyl)propane-2,2; 5.65 g. (25 mmol.) of bis(2,2,2-fluoroethyl) carbonate, and 1.0 mg. (0.02 mmol.) of sodium methoxide. The mixture was stirred in 10 ml. of solvent, e.g. toluene, while heating to the boiling point of the solvent while following progress of the reaction by thin layer chromatographic analysis. The reaction was terminated before buildup of oligomers occurred. The product consisted of BPA and a monocarbonate 2-(4-hydroxyphenyl)-2-[4-(2,2,2-trifluoroethyl)carbonyldioxy]-propane, of the formula:

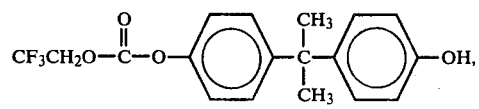

and a bis-carbonate, 2,2-bis(4-[2,2,2-trifluoroethyl]carbonyldioxy)propane, of the formula:

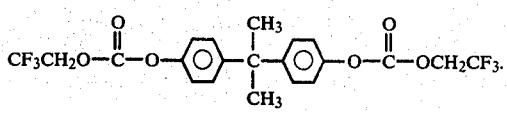

Separation by preparative high pressure liquid chromatography gave pure bis-carbonate in 60% yield (1.467 g.).

EXAMPLE III

A 100 ml. flask was charged with 11.414 g. of bisphenol-A (50.0 mmol.), 45.2 g. of bis(2,2,2-trifluoroethyl) carbonate (100 mmol.), and 1.0 mg. of lithium hydride (0.125 mmol., 0.25% relative to BPA). o-Dichlorobenzene was added, and the reaction mixture was heated to 120° C., temperature was maintained at 120° C. while trifluoroethanol distilled. After ½ hr., the temperature was raised slowly to 180° C. and a moderate vacuum was applied (100 mm. Hg.). After 1 hr., the reaction was terminated. Dissolution of the resulting reaction product in methylene chloride, i.e. $CH_2Cl_2$, and precipitation with methanol gave 12.736 g. of a white powder (99.5%). The polycarbonate had a weight average molecular weight, $\overline{M}_w$, of 17,500 (measured by gpc relative to a polystyrene standard). Further heating at 250° C. under high vacuum (1 mm. Hg.) raised the $\overline{M}_w$ to 44,000—again relative to the polystyrene standard.

EXAMPLE IV

A 100 ml. flask was charged with 4.56 g. of bisphenol-A (20.0 mmol.), 18.17 g. of bis(2,2,2-trifluoroethyl) carbonate (80.0 mmol.), and 0.001 g. of lithium hydride (0.125 mmol.). The mixture was heated with solvent. At 100° C. solution occurred. The reaction mixture was then heated at 120° C. for ½ hr. at atmospheric pressure. Vacuum (40 mm. Hg.) was applied for ½ hr., followed by high vacuum (1 mm. Hg.) for ½ hr., concurrent with heating to 190° C. Dissolution of the resulting reaction product in methylene chloride and precipitation with methanol gave 5.05 g. of white prepolymer (99.5%) having a $\overline{M}_w$ of 8300. Heating of the prepolymer at 250° C. for ½ hr. under still higher vacuum (0.10 mm. Hg.) gave colorless high molecular weight polymer having a $\overline{M}_w$ of 43,000 relative to a polystyrene standard. Additional heating at 300° C. for ½ hr. at 0.1 mm. Hg. gave colorless polymer having a $\overline{M}_w$ of 64,300 relative to the same polystyrene standard.

Aromatic high molecular weight polycarbonates, as illustrated by the foregoing Examples, advantageously can be prepared by our process. In general, presently commercially desirable high molecular weight polycarbonates exhibit a lower intrinsic viscosity of at least 0.3 and more preferably 0.5 deciliters per gm. (dl./g.) and an upper intrinsic viscosity generally equal to or less than 1.5 (dl./g.) as measured in either methylene chloride or chloroform or similar solvent systems at 25° C. Generally, especially useful polycarbonates, e.g. those derived from polyhydroxy compounds belonging to the class defined by formulas VI and VII set out hereinbefore have intrinsic viscosities within the range of from about 0.38 to about 0.7 (dl./g.). Preferred polycarbonates derived from such dihydroxy aromatic reactants have a sufficient number of the repeating units—as represented by the recurring subscript "n" of formula I—to give a number average molecular weight ($\overline{M}_w$) of at least about 5,000, and more preferably about 10,000 to about 50,000. Polycarbonates of this type are well-known and process easily at temperatures of at least 450° to 650° F. and have a wide variety of commercial uses well-known to those of ordinary skill in the art.

The transesterification process described herein is advantageously employed in the preparation of high molecular weight polycarbonates since the process is highly selective and efficient in the production of polycarbonates in the substantial absence of deleterious side reactions, e.g. decomposition of β-fluoroaliphatic carbonate reactant or the resulting polycarbonates.

In a presently preferred embodiment, the process is carried out by reacting a highly volatile low temperature boiling β-fluoroaliphatic carbonate with an aromatic polyhydroxy reactant, e.g. bis(4-hydroxyphenyl)-propane-2,2—also known as bisphenol-A, of formulas VI or VII, under reaction conditions wherein β-fluoroalkanols are readily removed from the reaction environment, i.e. evaporation or vaporization continuously as the high molecular weight polycarbonate process is carried to completion.

Further, as generally described in Equation I, set out herein, the process is broadly applicable in the preparation of aliphatic, cycloaliphatic and aromatic polycarbonates including combinations thereof based on reaction mixtures containing both and various aromatic and/or aliphatic dihydroxy compounds. The polycarbonates also can be prepared in any forms of, including random, alternating, and/or block, polycarbonates well-known to those skilled in the art.

Further, also included in the process is the preparation of low molecular weight polycarbonate dimers, trimers, oligomers, etc., i.e. polycarbonates containing at least two carbonate moieties.

Although the above examples have illustrated various modifications and changes that can be made in carrying out the process, it will be apparent to those skilled in the art that other changes and modifications can be made in the particular embodiments of the invention described which are within the full intended scope of the invention defined by the appended claims.

We claim:

1. A polycarbonate process comprising contacting in the presence of a base, a β-fluoroaliphatic carbonate, and a polyhydroxy compound selected from alcohols and/or phenols.

2. A claim 1 process wherein, (A) the β-fluoroaliphatic carbonate contains at least two oxy groups both independently and directly bonded to the same carbonyl carbon atom subject to the proviso that at least one of the oxy groups is separated from at least one fluorine atom by at least two aliphatic carbon atoms; (B) the alcohol is of the formula $R_a$-(OH)$_x$, wherein $R_a$ represents an aliphatic radical and —OH radicals are attached directly to aliphatic ring carbon atoms, x being a number at least equal to 2; and (C) the phenol is of the formula $R_b$-(OH)$_x$, wherein $R_b$ represents an aromatic radical and —OH radicals are attached directly to aromatic ring carbon atoms, x being a number at least equal to 2.

3. The claim 2 process wherein, (B) the alcohol is of the formula $C_nH_{2n+2-z}$, n is a whole number of from 1–30, and z is a whole number of from 2–4; and (C) the phenol is of the formula

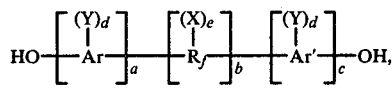

wherein $R_f$ is an alkylene, alkylidene, cycloalkylene, cycloalkylidene or arylene linkage or a mixture thereof, a linkage selected from the group consisting of ether, carbonyl, amine, a sulfur or phosphorus containing linkage, Ar and Ar' are arene radicals, Y is a substituent selected from the group consisting of organic, inorganic and organometallic radicals, X is halogen or a monovalent hydrocarbon group selected from the class consisting of alkyl, aryl and cycloalkyl and combinations thereof, d represents a whole number of at least 0 up to a maximum equivalent to the number of replaceable hydrogens substituted on the aromatic rings comprising Ar or Ar', e represents a whole number of from 0 to a maximum controlled by the number of replaceable hydrogens on $R_f$, a, b and c represent whole numbers including 0, when b is not zero, neither a or c may be zero, otherwise either a or c but not both may be 0, when b is zero, the aromatic groups can be joined by direct carbon bonds.

4. The claim 3 process wherein, (C) the phenols are of the formulae

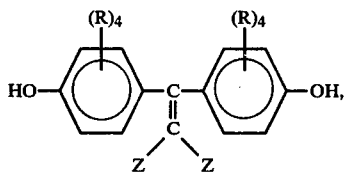

where independently each R is hydrogen, chlorine, bromine or a $C_{1-30}$ monovalent hydrocarbon or hydroxycarbonoxy group, each Z is hydrogen, chlorine or bromine, subject to the proviso that at least one Z is chlorine or bromine, or

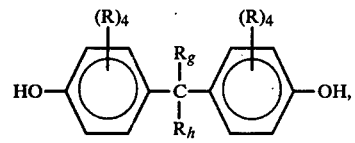

where independently each R is as defined hereinbefore, and independently $R_g$ and $R_h$ are hydrogen or a $C_{1-30}$ monovalent hydrocarbon group.

5. The claim 4 process wherein, (A) the β-fluoroaliphatic carbonates contain from 4–25 carbon atoms.

6. The claim 5 process wherein, (A) the β-fluoroaliphatic carbonate is selected from

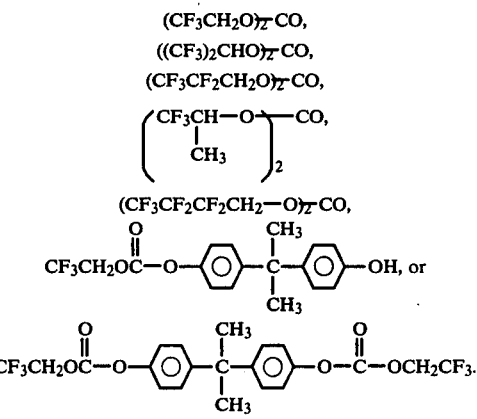

7. The claim 6 process wherein the process is carried out at a temperature within the range of from 80°–300° C. and within a pressure range including atmospheric to subatmospheric pressures.

8. The claim 7 process wherein at least a portion of a β-fluoroalkanol is withdrawn from the reaction medium to facilitate the formation of a high molecular weight aromatic polycarbonate.

9. The claim 8 process wherein the β-fluoroaliphatic carbonate is bis(2,2,2-trifluoroethyl) carbonate and the phenol is bis(4-hydroxyphenyl)propane-2,2.

10. The claim 9 process wherein the polycarbonate product of the process has a weight average molecular weight of from about 10,000 to about 50,000.

* * * * *